United States Patent [19]

Hergeth

[11] Patent Number: 4,881,415

[45] Date of Patent: Nov. 21, 1989

[54] DEVICE AND METHOD FOR HIGHLY ACCURATE MEASUREMENT OF THE THICKNESS OF FIBER MATS

[76] Inventor: Hubert Hergeth, Kockerellstrasse 3, 5100 Aachen, Fed. Rep. of Germany

[21] Appl. No.: 164,107

[22] Filed: Mar. 4, 1988

[30] Foreign Application Priority Data

Mar. 13, 1987 [DE] Fed. Rep. of Germany ....... 3708186

[51] Int. Cl.⁴ .............................................. G01B 5/06
[52] U.S. Cl. ..................... 73/865.8; 73/159; 364/563; 364/571.04
[58] Field of Search .................. 73/1 J, 1 R, 159, 104, 73/105, 865.8; 364/563, 571.01–571.08

[56] References Cited

U.S. PATENT DOCUMENTS

| | | | |
|---|---|---|---|
| 3,545,087 | 12/1970 | Doyle, III et al. | 73/1 J X |
| 3,769,829 | 11/1973 | Fleming, Jr. et al. | 73/1 R |
| 4,213,319 | 7/1980 | Gold et al. | 33/143 L X |
| 4,404,634 | 9/1983 | Bautz | 73/159 X |
| 4,420,747 | 12/1983 | Kistner | 340/67.4 |
| 4,426,239 | 1/1984 | Upmeier | 73/159 X |
| 4,491,929 | 1/1985 | Ikoma et al. | 364/563 |
| 4,525,315 | 6/1985 | Greten | 73/159 X |
| 4,562,730 | 1/1980 | Gowman | 73/159 X |
| 4,578,052 | 3/1986 | Engel et al. | 73/159 X |
| 4,623,835 | 11/1986 | Meldizadeh et al. | 313/61 R X |
| 4,662,209 | 3/1987 | Brown | 73/1 J X |
| 4,674,310 | 6/1987 | Ginzburg | 73/159 X |
| 4,676,094 | 6/1987 | Hoffmann et al. | 73/159 X |
| 4,682,105 | 7/1987 | Thorn | 73/159 X |
| 4,700,368 | 10/1987 | Munn et al. | 340/674 X |
| 4,815,015 | 3/1989 | Milne | 364/563 |

FOREIGN PATENT DOCUMENTS 3205776 8/1983 Fed. Rep. of Germany .
3315909 4/1988 Fed. Rep. of Germany .

OTHER PUBLICATIONS

"Die moderne Baumwollspinnerei" (Modern Methods of Cotton Spinning) by Prof. Dr. Ing. Fritz Walz, Bernh. Friedr. Voigt, Verlag Handwerk und Technik, Berlin–Hamburg, pp. 90–92, published 1960.

Primary Examiner—Tom Noland
Attorney, Agent, or Firm—Herbert Dubno

[57] ABSTRACT

The profile of a measurement roll is stored in a computer during a calibration revolution. On revolution with fiber mats to be measured, the computer reduces the measured values exactly by the measured values of the corresponding calibration profile. The measurement result obtained does not depend on the production quality of the measurement roll.

5 Claims, 3 Drawing Sheets

DEVICE AND METHOD FOR HIGHLY ACCURATE MEASUREMENT OF THE THICKNESS OF FIBER MATS

FIELD OF THE INVENTION

This invention relates to a method of and an apparatus for measurement of the thickness of a fiber mat.

BACKGROUND OF THE INVENTION

In the textile industry, fibers are collected and compacted continuously in hoppers for subsequent feeding to a downstream processing machine such as a beater or card.

It is of great importance for further processing that the fiber mat should have a satisfactory regularity; a number of devices and circuits for measurement and consequent control have therefore already been disclosed and are used extensively in the textile industry. Most of these devices comprise a conveying roll, which is preferably of fluted design for the purpose of conveying the fiber efficiently, a plurality of movable contact-pressure noses, so-called pedal noses, and an electrical evaluation device. A device of this kind is described in Walz, "Die moderne Baumwollspinnerei", (Modern Methods of Cotton Spinning), 1960, page 91. German Patent DE No. 3,205,776 shows a further refinement of this method of measurement.

All methods of measurement by means of a roll and a pedal nose to date depend on the trueness of the roll. In this case of fluted rolls, measurement errors additionally occur by reason of the fluting. If measurements over large widths, e.g. 4 m, and precision of the measured values over the width are required, such measurement rolls become very expensive to produce. Accuracies should be within the range of 1/1000 mm. To date it has been impossible to take into account differing sagging behaviors of welding tubes which have been used as such rolls.

It is the object of the invention to provide an improved method of and an inexpensive apparatus for the accurate measurement of the thickness of mats.

SUMMARY OF THE INVENTION

According to the invention, highly accurate measurement is achieved by determining individual measuring points or areas on the measurement roll and storing the pedal measurement values in the absence of material during a calibration revolution of the roll in a stored-program control.

Subsequently, in the case of measurement with material, the pedal measurement values obtained with material are reduced by the stored values and the actual measurement values are thus obtained.

By way of example, the measuring device comprises a measurement roll, for pedal noses, four displacement transducers, three position transmitters and a stored-program control. The commercially available stored-program control has digital and analog high-resolution inputs and outputs. The four displacement transducers measure the deflection of the pedal noses. This can be done, for example, inductively, capacitively or by other suitable displacement measurements. The measured values are fed to the control as digital or analog values 0–10 V or 0–20 mA. The rotational position of the roll, e.g. 0, 120 degrees, 240 degrees is determined by three metal lugs, which are attached to the roll and revolve with the measurement roll. The three digital transducers, e.g. proximity switches, are fixed. The angular position of the roll can also be communicated to the stored-program control by an analog position transmitter or digital coding.

The measurement roll does not require any special treatment for measuring purposes. The system is caibrated in the absence of material. The measurement roll rotates. Once an angular position has been reached, e.g. 240 degrees, the angle transmitter passes a signal to the stored-program control. The stored-program control then requests the calibration values for the pedal noses from displacement transducers. The respective values are digitalized and stored.

The following values are stored: A-II-E; B-II-E; C-II-E; D-II-E.

The initial indices A-, B-, C-, and D indicates the position along the roll, the Roman numerals (II), for example, stand for the angular position and the final letter indices, E- for example, stand for calibration values. On further totation of the roll, the position 0/360 is reached and the values A-I-E; B-I-E; C-I-E; D-I-E are stored. On further rotation, the values A-III-E; B-III-E; C-III-E; D-III-E are in addition also stored. Once all these values have been stored, the calibration operation is complete and the measurements with material can begin. In the case of material throughput, the measurement roll rotates; once the rotational position 0/360 has been reached, the computer requests the measured values and receives the actual values A-I-I; B-I-I; C-I-I; D-I-I where the final index I represents the actual value measurement.

This request takes place within a few hundredths of a second. The measured values are put into intermediate storage and the corresponding calibration values are subtracted from the actual values. The result corresponds to the measured value (M).

$$(A\text{-I-I}) - (A\text{-I-E}) = A - M$$
$$(B\text{-I-I}) - (B\text{-I-E}) = B - M$$
$$(C\text{-I-I}) - (C\text{-I-E}) = C - M$$
$$(D\text{-I-I}) - (D\text{-I-E}) = D - M$$

The resulting measured values are used for control purposes as explained in German Patents DE No. 3,205,776 or DE No. 3,315,909. On further rotation of the roll, rotational position II is reached and the measured values (A-II-I); (B-II-I); (C-II-I); (D-II-I) are read in by the computer.

The calibration values can then be subtracted to obtain the new measured values.

$$(A\text{-II-I}) - (A\text{-II-E}) = A - M$$
$$(B\text{-II-I}) - (C\text{-II-E}) = B - M$$
$$(C\text{-II-I}) - (C\text{-II-E}) = C - M$$
$$(D\text{-II-I}) - (D\text{-II-E}) = D - M$$

On further rotation of the roll, at position III, the actual values III are again entered by the SPC and the subtraction by the calibration values III is then carried out to obtain the measured values. On further rotation, the throughput begins again at position I.

In this way, a very accurate measurement of the fiber mat can be carried out, even with an inaccurately produced measurement roll. The outlay for greater stored-program control capacity, it at all necessary, is insignificant compared with the production costs saved.

This type of measurement has the further advantage of compensating for wear or displacement of the measuring device.

If the measured values are only required at relatively large intervals, it is possible to fit less than three sensing positions at the periphery of the roll. The number of measuring points along the roll varies with the number of pedal noses employed. It is not necessary for the roll positions and those of the pedals to be distributed in a regular manner.

If, in another arrangement of the displacement sensor, the measured value is reduced for fiber throughput, the calibration values are added to the actual value to obtain the measured value.

BRIEF DESCRIPTION OF THE DRAWING

The above and other objects, features and advantages of the present invention will become more readily apparent from the following description, reference being made to the accompanying drawing in which.

DESCRIPTION

Figure 1:
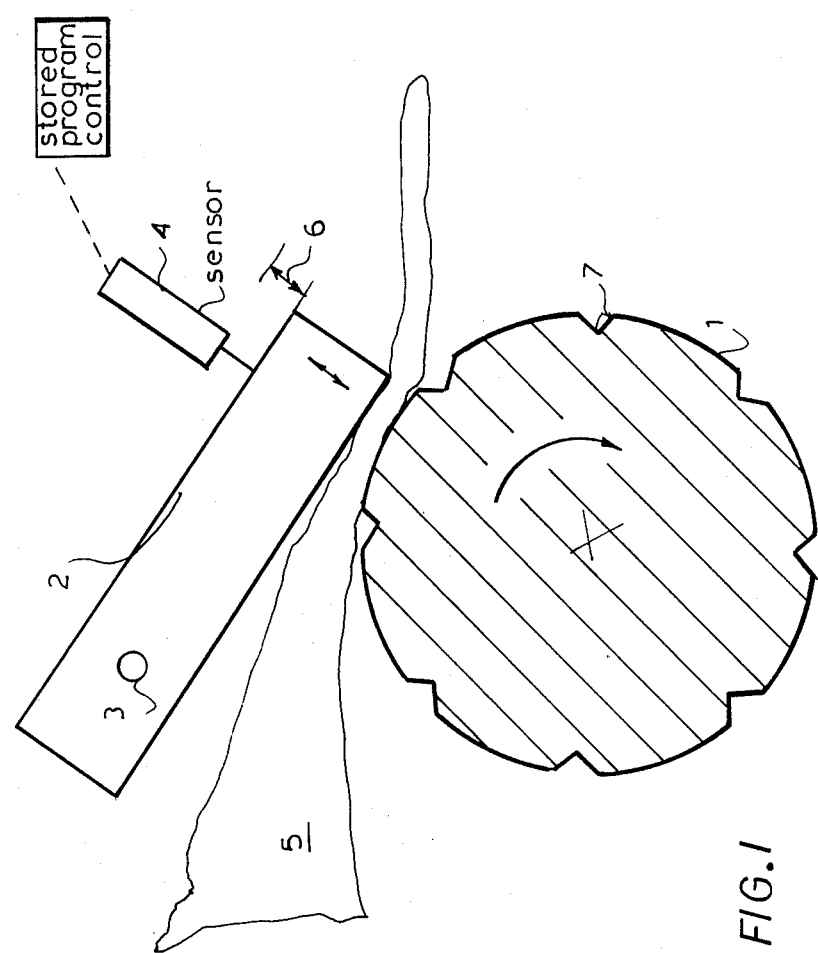
FIG. 1 is a diagrammatic sectional view.

FIG. 1 shows a diagrammatic cross-section through the measuring device in which a fiber mat 5 is passed between a measurement roll 1 and a pedal 2. The varying thickness of the fiber mat causes the pedal to swing about the pivot point 3. The change in the position of the pedal is detected by the sensor 4 as interval 6.

For better fiber transport, the measurement roll is provided with flutes 7.

Figure 2:
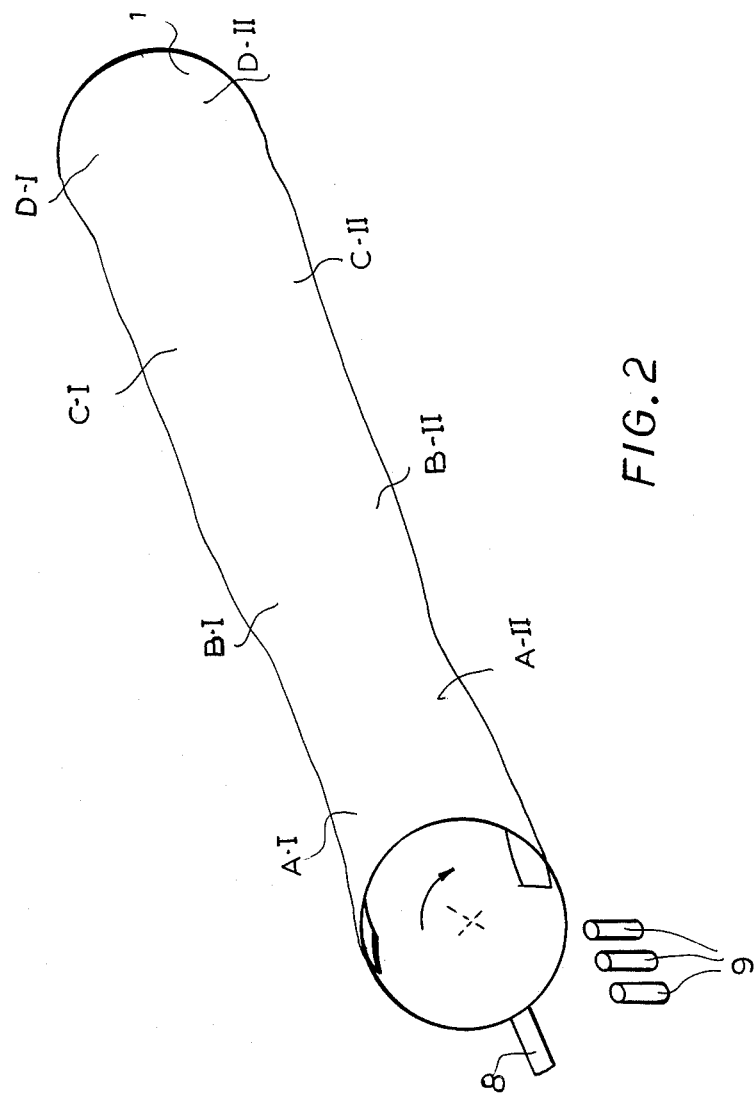
FIG. 2 is a diagrammatic perspective view illustrating the invention.

FIG. 2 shows a measurement roll diagrammatically. Switching lugs 8 for detecting the angle of rotation by the switch 9 are attached to the measurement roll. The inexact production is made clear by the wavy contour. The distribution of the measuring zones AI-CII on the measurement roll is shown.

Figure 3:
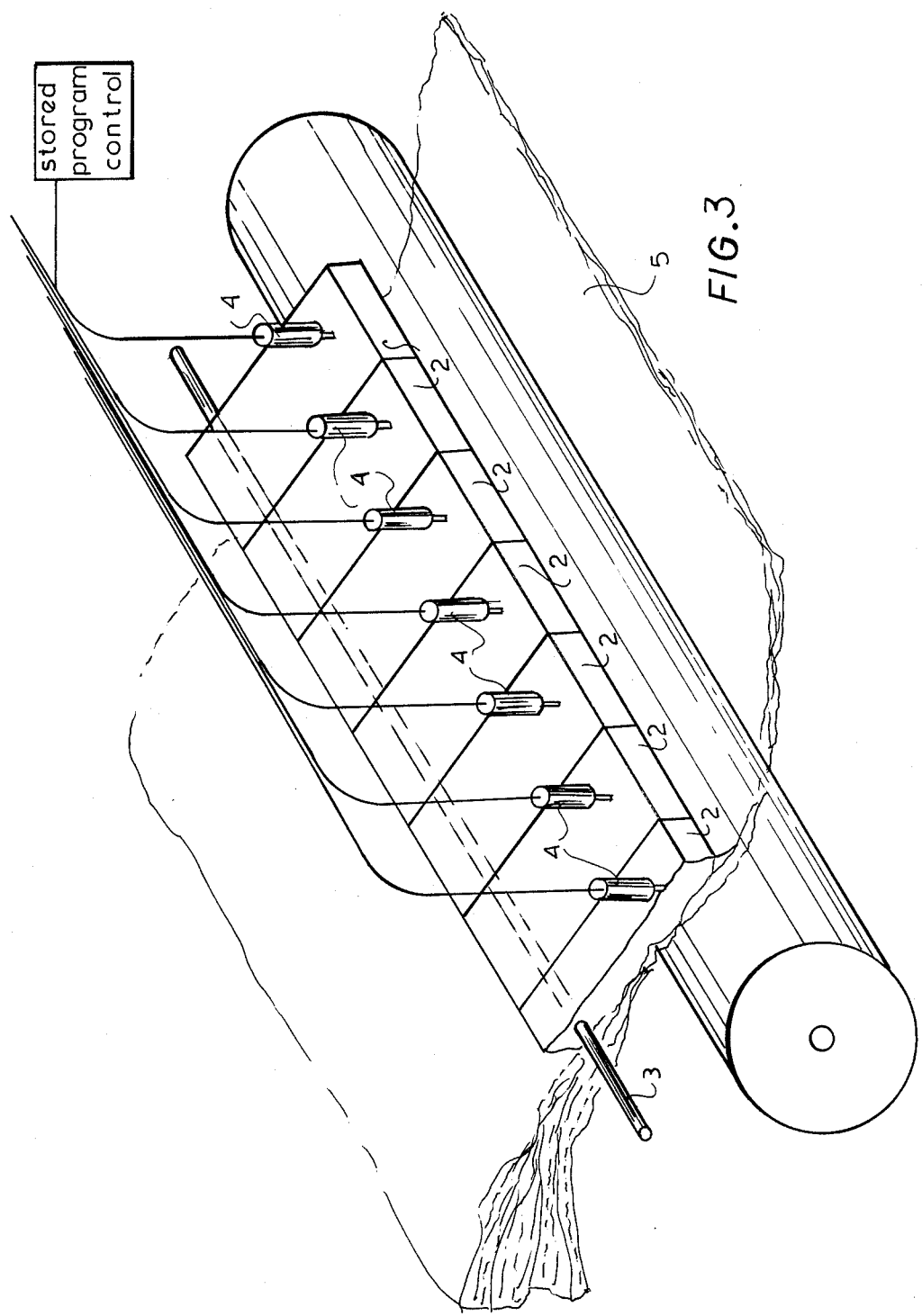
FIG. 3 is a perspective view of another embodiment.

FIG. 3 shows an embodiment of the invention in which the feelers 2 are axially spaced along the roll 1 and the mat 5 passes between these feelers and the roll. The feelers 2 are swingable about that pivot point 3 and the change in the position of the feelers is detected by the sensors 4.

What is claimed is:

1. A method of measuring the thickness of a fiber mat comprising the steps of:
   (a) rotating a roller, having a circumference over which a fiber mat is adapted to pass, about an axis of said roller;
   (b) at each of a plurality of locations axially spaced apart on said circumference with respective feelers adapted to contact said circumference, generating measured values of displacement of said feelers for each of a plurality of angular positions of said roller during a calibration revolution thereof;
   (c) storing each of said values as respective calibration values corresponding to locations upon said circumference;
   (d) thereafter passing said fiber mat between said feelers and said circumference by rotating said roller, thereby advancing said mat while said feelers are displaced by said mat;
   (e) measuring an actual value of displacement of each of said feelers by said mat for each of said locations upon rotation of said roller; and
   (f) correcting an actual value as measured in step (e) with the respective stored value for respective locations to obtain actual measurements of thickness of said mat.

2. The method defined in claim 1 wherein the correction in step (f) is effected by subtracting from a measured actual value of displacement in step (e), a stored calibration value corresponding to the respective location upon said circumference.

3. The method defined in claim 1 wherein said locations are distributed over the periphery of said roller.

4. The method defined in claim 1 wherein said values are obtained by measuring deflection of said feelers.

5. An apparatus for measuring the thickness of a fiber mat, comprising:

a roller rotatable about an axis and having a circumference over which a fiber mat is adapted to pass;

respective feelers at axially-spaced locations axially spaced on said circumference adapted to contact said circumference and provided with respective sensors generating measured values of displacement of said feelers for each of a plurality of angular positions of said roller during a calibration revolution thereof;

a stored-program control connected to said sensors for storing each of said measured values of displacement as respective calibration values corresponding to locations upon said circumference;; and means for passing said fiber mat between said feelers and said circumference by rotation of said roller, thereby advancing said mat while said feelers are displaced by said mat so that said sensors produce actual values of displacement for each of said feelers by said mat for each of said locations and said stored-program control corrects an actual value of displacement of each of said feelers with a respective stored-calibration value for a respective location to yield actual measurements of thickness of said mat.

* * * * *